United States Patent
Milshtein

(10) Patent No.: US 7,619,735 B2
(45) Date of Patent: Nov. 17, 2009

(54) OPTICAL INSPECTION USING VARIABLE APODIZATION

(75) Inventor: Erel Milshtein, Cupertino, CA (US)

(73) Assignee: Applied Materials, Israel, Ltd., Rehov9t (IL)

( * ) Notice: Subject to any disclaimer, the term of this patent is extended or adjusted under 35 U.S.C. 154(b) by 271 days.

(21) Appl. No.: 10/342,566

(22) Filed: Jan. 14, 2003

(65) Prior Publication Data

US 2003/0137659 A1    Jul. 24, 2003

Related U.S. Application Data

(60) Provisional application No. 60/349,662, filed on Jan. 15, 2002.

(51) Int. Cl.
  *G01N 21/00* (2006.01)
(52) U.S. Cl. .................................................. 356/340
(58) Field of Classification Search ............. 356/237.1, 356/237.2–237.5, 239.7, 239.8; 250/559.4–559.49
See application file for complete search history.

(56) References Cited

U.S. PATENT DOCUMENTS

| | | | | |
|---|---|---|---|---|
| 3,614,232 A | | 10/1971 | Mathisen | |
| 4,844,617 A | * | 7/1989 | Kelderman et al. | 356/624 |
| 5,602,619 A | * | 2/1997 | Sogard | 355/53 |
| 5,659,168 A | * | 8/1997 | Dey et al. | 250/208.1 |
| 5,768,017 A | * | 6/1998 | King et al. | 359/559 |
| 5,859,424 A | * | 1/1999 | Norton et al. | 250/226 |
| 6,081,325 A | * | 6/2000 | Leslie et al. | 356/237.2 |
| 6,133,986 A | * | 10/2000 | Johnson | 355/67 |
| 6,177,980 B1 | * | 1/2001 | Johnson | 355/67 |
| 6,248,988 B1 | * | 6/2001 | Krantz | 250/201.3 |
| 6,459,484 B1 | * | 10/2002 | Yokoi | 356/318 |
| 6,466,315 B1 | * | 10/2002 | Karpol et al. | 356/237.4 |
| 6,540,145 B2 | * | 4/2003 | Gurevich et al. | 235/462.21 |
| 6,911,347 B2 | * | 6/2005 | Higgs | 438/7 |
| 6,950,194 B2 | * | 9/2005 | Sandstrom | 356/401 |
| 2003/0132405 A1 | | 7/2003 | Some | |

* cited by examiner

*Primary Examiner*—L. G Lauchman
*Assistant Examiner*—Juan D Valentin
(74) *Attorney, Agent, or Firm*—Tarek N. Fahmi

(57) ABSTRACT

A method for optical inspection of a surface includes selecting an apodization scheme in response to a characteristic of the surface, and applying an apodizer to apodize a beam of radiation in response to the selected apodization scheme. The apodized beam of radiation is directed to impinge on the surface, whereby a plurality of rays are scattered from the surface, and at least one of the scattered rays is detected, typically in order to detect a defect on the surface.

35 Claims, 10 Drawing Sheets

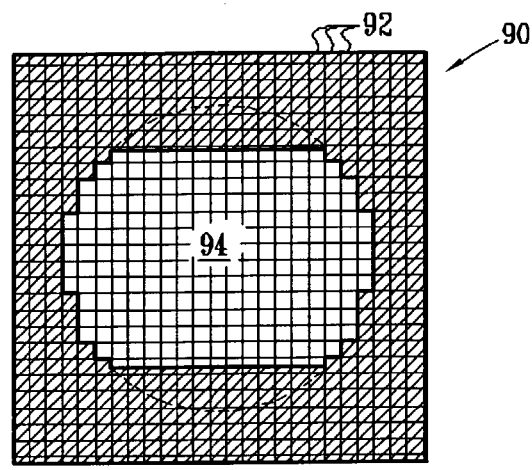
FIG. 6
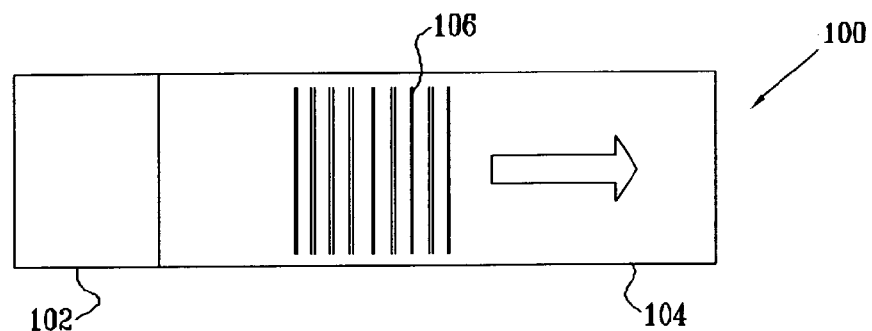
FIG. 7A
FIG. 7B
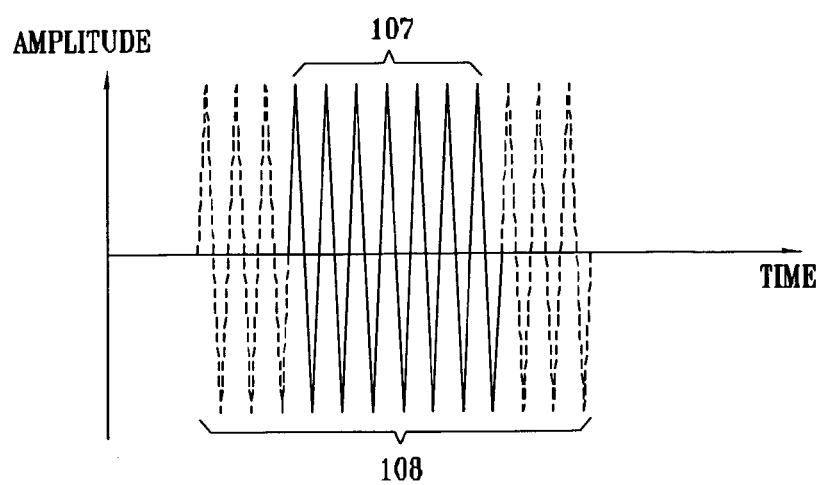

OPTICAL INSPECTION USING VARIABLE APODIZATION

CROSS-REFERENCE TO RELATED APPLICATION

This application claims the benefit of U.S. Provisional Patent Application No. 60/349,662, filed Jan. 15, 2002, which is incorporated herein by reference.

FIELD OF THE INVENTION

The present invention relates generally to methods and systems for automated optical inspection, and specifically to methods for enhancing sensitivity of optical inspection systems that are used for defect detection.

BACKGROUND OF THE INVENTION

Laser scanning systems are well known in the art of optical inspection. Typically, a laser beam scans over the substrate under inspection, and the light scattered from the substrate is collected by a detector. The intensity (and possibly other characteristics) of the scattered light is compared to an expected range of values. Deviations of the scattered light from the expected range can be indicative of defects in or on the substrate. In integrated circuit (IC) manufacturing, for example, as the laser beam scans the area of a given die on a wafer, the detector signal is compared to a reference signal from another die ("die-to-die" mode) or to stored reference values ("die-to-database" mode). Defects on the wafer are noted wherever the signal deviates from the reference.

The sensitivity of a defect detection system depends on its signal/noise ratio (SNR). In this context, the signal corresponds to the amount of light scattered from the defect that is able to reach the detector. The "noise" is generally dominated by background light that is reflected or otherwise scattered from the substrate itself. (In the context of the present patent application and in the claims, the term "scattered" refers to all radiation returned from the surface, due to substantially any physical mechanism, including diffractive scattering and both specular and diffuse reflection.) When a patterned semiconductor substrate is illuminated with coherent light, for example, the light is diffracted from the repetitive pattern and generates constructive interference lobes along well-defined directions. The positions and extent of the interference lobes depend on the period of the pattern, as well as the wavelength of the incident radiation and characteristics of the optical system.

It is known in the art that blocking the interference lobes can facilitate the detection of defects and pattern irregularities on the substrate. For example, U.S. Pat. No. 3,614,232, to Mathisen, whose disclosure is incorporated herein by reference, describes a spatial filter for detecting defects in photomasks, using a transmission geometry and a simple filter consisting substantially of the negative of the Fourier transform of a defect-free specimen of the microcircuit. There are many cases, however, in which the interference lobes occupy substantially the entire field of view of the detector, so that blocking the lobes is impossible without entirely blocking the detector. Even when a portion of the field of view of the detector is still available between the interference lobes, this portion may be so limited that too small a signal remains after blocking the regions of the lobes.

SUMMARY OF THE INVENTION

The present invention is based on the realization that the shapes of the interference lobes created by diffraction of coherent light from a patterned surface are determined by the shape of the spot of light that is incident on the surface. This shape may, in turn, be controlled by adjusting the entrance pupil, or aperture, through which the light is focused onto the surface. Therefore, it is possible to adjust the shapes and other characteristics of the interference lobes by appropriate control of the incident beam, known as apodization.

In embodiments of the present invention, an optical inspection system comprises a radiation source, such as a laser, which generates a beam of coherent radiation. The beam is focused through an aperture onto the patterned surface of a substrate under inspection. A detector collects light that is scattered from the surface. The aperture is selected in order to control characteristics of the lobes of radiation diffracted from the surface. Typically, the shape of the aperture is chosen so as to determine the extent to which the interference lobes fill the field of view of the detector, depending on the characteristics of the pattern on the surface that creates the lobes. A spatial filter is interposed between the surface and the detector in order to block the interference lobes, while allowing the scattered light (typically from defects on the surface) in between the lobes to reach the detector.

Proper selection of the characteristics of the aperture and the spatial filter permits the SNR of the detector to be optimized for each type of substrate pattern that the inspection system encounters. This optimization involves choosing the size and shape of the aperture so as to reduce the background level, typically by narrowing the aperture to decrease the extent of the interference lobes, while leaving a sufficient opening so that an adequate signal reaches the detector. The inspection system may be provided with an adjustable aperture or with a collection of different apertures, to be selected according to the substrate pattern and possibly other system requirements.

There is therefore provided, in accordance with an embodiment of the present invention, a method for optical inspection of a surface, including:

selecting an apodization scheme in response to a characteristic of the surface;

applying an apodizer to apodize a beam of radiation in response to the selected apodization scheme;

directing the apodized beam of radiation to impinge on the surface, whereby a plurality of rays are scattered from the surface; and detecting at least one of the scattered rays.

In an embodiment of the invention, selecting the apodization scheme includes setting a characteristic of an entrance pupil, and applying the apodizer includes passing the beam of radiation through the entrance pupil. Setting the characteristic may include providing a non-circular entrance pupil. Providing the non-circular entrance pupil may include placing an aperture having a generally rectangular shape in the entrance pupil, or placing a negative aperture in the entrance pupil. Additionally or alternatively, providing the non-circular entrance pupil may include placing an aperture having edges characterized by a smooth gradation of optical density in the entrance pupil.

Typically, providing the non-circular entrance pupil includes placing in the entrance pupil an aperture having a length dimension and a width dimension, wherein the length and width dimensions are not equal, and at least one of the length and width dimensions is set in response to a pitch of a pattern on the surface.

Alternatively or additionally, setting the characteristic of the entrance pupil includes offsetting the entrance pupil relative to an axis of the beam so as to adjust an angle of incidence of the beam on the surface.

In other embodiments, setting the characteristic includes placing an array of shutter elements in the entrance pupil, and controlling the shutter elements to set a shape of the entrance pupil, or providing a plurality of apertures, and choosing one of the apertures to place in the entrance pupil.

Typically, detecting the at least one of the scattered rays includes applying a spatial filter, in response to the selected apodization scheme, so as to select the at least one of the scattered rays to be detected. The surface may be characterized by a pattern that scatters the rays into one or more angular lobes, so that applying the spatial filter includes selecting the filter so as to block the rays in the one or more angular lobes, while allowing the at least one of the scattered rays to be detected in a region between the lobes. The apodization scheme may be chosen so as to limit an angular extent of the lobes, wherein choosing the apodization scheme includes setting an attribute of the apodizer in response to a pitch of the pattern.

In an embodiment of the present invention, detecting the at least one of the scattered ray includes measuring the at least one of the scattered rays in order to identify a defect in the pattern.

In a further embodiment, directing the apodized beam includes scanning the apodized beam over the surface, and detecting the at least one of the scattered rays includes detecting the rays scattered from multiple points on the surface that are scanned by the beam. Applying the apodizer may include driving an optical modulator to serve as a traveling lens in synchronization with scanning the beam, so as to apodize the beam as it scans over the surface.

In another embodiment, when the surface is characterized by scattering structures disposed along a predetermined direction, selecting the apodization scheme includes configuring the apodizer so that the apodized beam of radiation impinging on the surface forms a non-circular spot, having a long axis substantially parallel to the predetermined direction.

In yet another embodiment, applying the apodizer includes focusing the beam of radiation onto the surface with a first numerical aperture (NA) along a first transverse axis and a second NA along a second transverse axis, perpendicular to the first transverse axis, such that the first NA is substantially different from the second NA.

In embodiments of the present invention, directing the apodized beam includes causing the beam to irradiate the surface in at least one of a normal incidence direction and an oblique incidence direction, and detecting the at least one of the scattered rays includes configuring a detector to receive the at least one of the scattered rays in a dark field detection configuration, along at least one of a normal collection axis and an oblique collection axis.

There is also provided, in accordance with an embodiment of the present invention, a method for optical inspection, including:

providing an inspection system with an apodizer capable of implementing a plurality of apodization schemes;

selecting one of the apodization schemes;

applying the apodizer to apodize a beam of radiation in response to the selected apodization scheme;

directing the apodized beam of radiation to impinge on the surface, whereby a plurality of rays are scattered from the surface; and detecting at least one of the scattered rays.

There is additionally provided, in accordance with an embodiment of the present invention, a method for optical inspection of a surface having a pattern formed thereon, the method including:

directing a beam of radiation through an entrance pupil so as to impinge on the surface, whereby a plurality of rays are scattered from the surface, including multiple rays scattered by the pattern into one or more angular lobes;

configuring the entrance pupil with a non-circular aperture, so as to limit an angular extent of the angular lobes along a selected angular direction;

applying a spatial filter so as to block the rays in the one or more angular lobes; and receiving at least one of the scattered rays that is not blocked by the spatial filter, so as to detect a defect in the pattern.

Typically, configuring the entrance pupil includes setting a length dimension of the entrance pupil to be different from a width dimension of the entrance pupil, so that the angular lobes do not substantially overlap with other, adjacent lobes along the selected angular direction.

There is further provided in accordance with an embodiment of the present invention, apparatus for optical inspection of a surface, including:

a radiation source, which is adapted to generate a beam of coherent radiation;

a variable apodizer, which is adapted to apodize the beam in response to a selected apodization scheme;

an optical objective, which is adapted to direct the apodized beam of radiation to impinge on the surface, whereby a plurality of rays are scattered from the surface; and a detector, which is adapted to detect at least one of the scattered rays.

In an embodiment of the invention, the apparatus includes a scanner, which is adapted to scan the apodized beam over the surface, and the detector is adapted to detect the at least one of the scattered rays from multiple points on the surface that are scanned by the beam. The apodizer may include an optical modulator, which is configured to serve as a traveling lens in synchronization with the scanner, so as to apodize the beam as it scans over the surface.

Additionally or alternatively, the apodizer may include a focusing device, which is adapted to cause the beam of radiation to be focused onto the surface with a first numerical aperture (NA) along a first transverse axis and a second NA along a second transverse axis, perpendicular to the first transverse axis, such that the first NA is substantially different from the second NA.

There is moreover provided, in accordance with an embodiment of the present invention, apparatus for optical inspection of a surface, including:

a radiation source, which is adapted to generate a beam of coherent radiation;

an optical objective, which is adapted to direct the apodized beam of radiation to impinge on the surface, whereby a plurality of rays are scattered from the surface, including multiple rays scattered by the pattern into one or more angular lobes;

a non-circular aperture, located at an entrance pupil of the optical objective, the aperture having a dimension that is chosen so as to limit an angular extent of the angular lobes along a selected angular direction;

a spatial filter, which is configured to block the rays in the one or more angular lobes; and a detector, which is adapted to receive at least one of the scattered rays that is not blocked by the spatial filter, so as to detect a defect in the pattern.

In an embodiment of the invention, the detector is adapted to generate a signal in response to the at least one of the scattered rays, and the apparatus includes a processor, which is adapted to measure the signal in order to identify a defect in the pattern.

The present invention will be more fully understood from the following detailed description of the embodiments thereof, taken together with the drawings in which:

BRIEF DESCRIPTION OF THE DRAWINGS

FIG. 6 is a schematic frontal view of a shutter array used to apodize a beam of radiation in an optical inspection system, in accordance with an embodiment of the present invention;

FIG. 7A is a schematic frontal view of an acousto-optic device used to apodize a beam of radiation in an optical inspection system, in accordance with an embodiment of the present invention;

FIG. 7B is a schematic plot of a driving waveform applied to the acousto-optic device of FIG. 7A in order to apodize the beam of radiation;

DETAILED DESCRIPTION OF EMBODIMENTS

Figure 1:
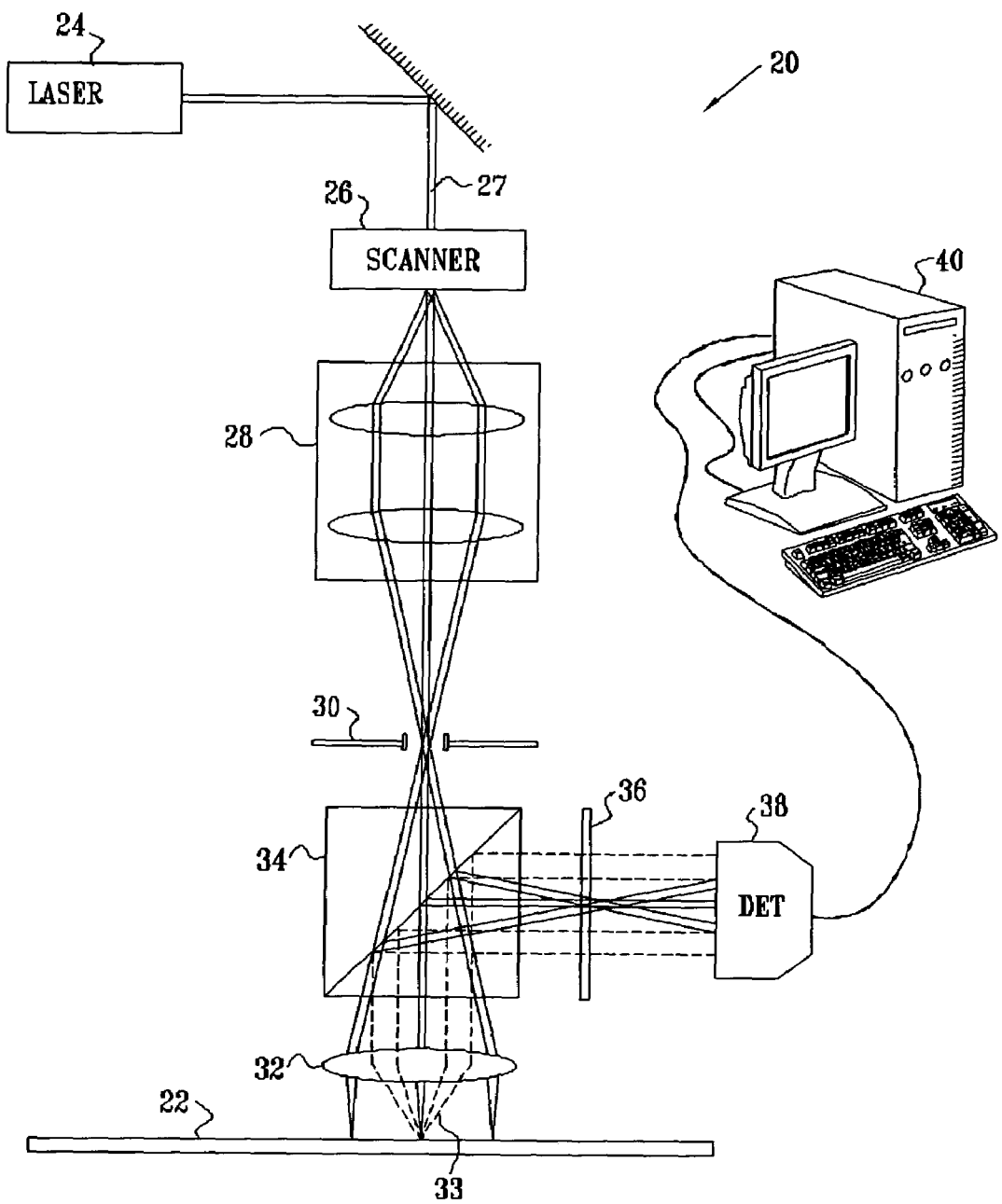
FIG. 1 is a schematic side view of an optical inspection system, in accordance with an embodiment of the present invention.

FIG. 1 is a schematic side view of a system 20 for optical inspection of a substrate 22, in accordance with an embodiment of the present invention. System 20 is designed for detecting defects in integrated circuit (IC) wafers, and applies apodization techniques, as described hereinbelow, that are particularly useful in suppressing background scattering due to patterns formed on the wafer surface. Patterns of this sort are encountered in many types of ICs, but particularly in memory devices, such as SRAM and DRAM chips. Therefore, in the description that follows of system 20 and of various apodization schemes that can be used in the system, reference is made to such patterns. It should be understood, however, that these references to IC patterns are made by way of example, and the principles of the present invention may similarly be applied to inspection of surfaces of other types. In particular, the principles of system 20 may be applied, mutatis mutandis, to inspection of lithographic masks used in IC production, as well as other patterned surfaces, including flat panel displays, such as liquid crystal devices.

System 20 comprises a laser 24 or other source of coherent radiation. A scanner 26, typically an acousto-optic device or rotating mirror, as are known in the art, deflects a laser beam 27 along a scan direction. Relay optics 28 direct the beam through an entrance pupil 30, and a scan objective 32 focuses the beam onto the surface of substrate 22. The incident laser light is scattered from the surface, generating scattered radiation 33, a portion of which is collected by objective 32. A beamsplitter 34 directs the scattered radiation onto a detector 38 via a spatial filter 36. The spatial filter is chosen, in conjunction with the shape and other characteristics of the incident beam, so as to block rays of background radiation, including the specular reflection of incident beam 27, while still allowing at least some of the signal rays to reach the detector.

In the context of the present patent application and in the claims, the choice of incident beam shape (and possibly other ancillary characteristics, such as the incident angle of the beam on substrate 22 and the phase profile across the beam) and the method of creating the desired shape are referred to as an "apodization scheme." The element used to impose the desired apodization on the incident beam is referred to herein as an "apodizer." In most of the embodiments described hereinbelow, the apodizer comprises a suitable aperture placed at entrance pupil 30. Beam 27 is thus apodized by appropriate selection of the shape, dimensions and other characteristics of the aperture, including its position with respect to the scan axis (which affects the incident angle of the beam on substrate 22). Other types of apodizers may also be used, however, such as a traveling wave lens, shown below in FIG. 7. In any case, the apodization scheme can be chosen in such a way as to suppress interference lobes created by regular patterns on the surface of the substrate, as are formed on many IC structures, while allowing at least some of the radiation that is scattered from defects on the surface to reach detector 38 through an appropriately chosen filter 36. Exemplary apodization schemes for this purpose are described hereinbelow.

The signal output by detector 38 is received by a signal processor 40, typically a general-purpose computer with suitable front end circuits and software. Processor 40 analyzes the signal in order to locate and identify scattering features, such as defects, on the surface. The apodization scheme may be chosen, as described below, in order to optimize the SNR of the signal received by processor 40. Such optimization involves finding the optimal tradeoff between strength of the signal due to the scattering features of interest and strength of the background due to the regular pattern on the surface.

Figure 2A:
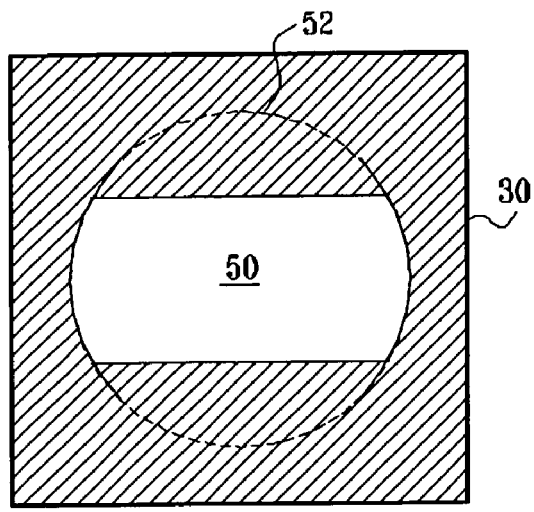
FIG. 2A is a schematic frontal view of an aperture used to apodize a beam of radiation in an optical inspection system, in accordance with an embodiment of the present invention.
Figure 2B:
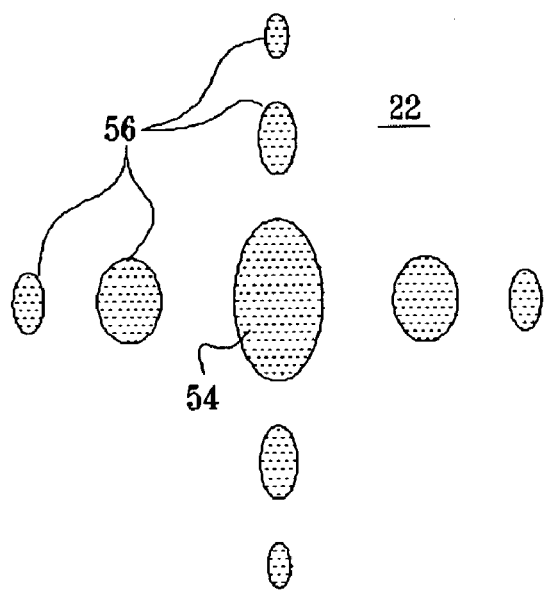
FIG. 2B is a schematic top view of a substrate on which the beam apodized by the aperture of FIG. 2A is incident, showing a pattern of the radiation that is incident on the substrate.

Reference is now made to FIGS. 2A and 2B, which schematically show details of an apodization scheme that can be used in system 20, in accordance with an embodiment of the present invention. FIG. 2A illustrates an aperture 50 used as an apodizer in entrance pupil 30, while FIG. 2B shows a pattern of spots 54 and 56 formed on the surface of substrate 22 due to focusing of the laser beam through aperture 50. The pattern shown in FIG. 2B is a spatial Fourier transform of the shape of aperture 50, including central spot 54 corresponding to the central lobe of the transform function, and peripheral spots 56 due to the side lobes. A circle 52 in FIG. 2A represents the shape of a corresponding circular aperture, as is used in inspection systems known in the art. The effect of narrowing aperture 50, relative to circle 52, is to increase the size of central spot 54 in the direction of narrowing (i.e., the vertical direction in FIGS. 2A and 2B), relative to the spot that would by created by the circular aperture. As a result of the increased spot size and reduced aperture area, the intensity of the radiation scattered from the substrate is reduced, as well, thus reducing the amplitude of the signal output by detector 38.

Figure 3A:
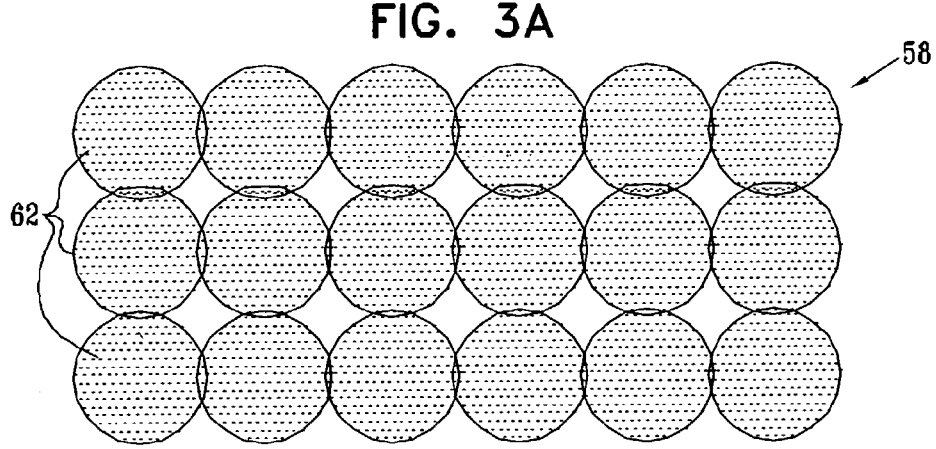
FIG. 3A is a schematic frontal view of an interference pattern created by radiation reflected from a substrate using circular apodization.

FIG. 3A is a schematic frontal view of a pattern 58 of interference lobes 62, created due to diffraction from a repetitive structure on substrate 22 when an aperture in the shape of circle 52 is used at entrance pupil 30. Pattern 58 is created in the Fourier plane of objective 32, where filter 36 is located. The shape of lobes 62 is determined by the shape of aperture 50. The spacing of lobes 62 is determined by the optical characteristics of system 20 and by the pitch (horizontal and vertical) of the structure on the substrate. The larger the pitch, the closer is the spacing of lobes 62. In the example shown in FIG. 3A, lobes 62 overlap with their neighbors in both horizontal and vertical directions, covering nearly the entire field of view of detector 38. Therefore, it becomes virtually impossible for filter 36 to block the background radiation in lobes 62 and still enable a significant scattering signal to reach the detector.

Figure 3B:
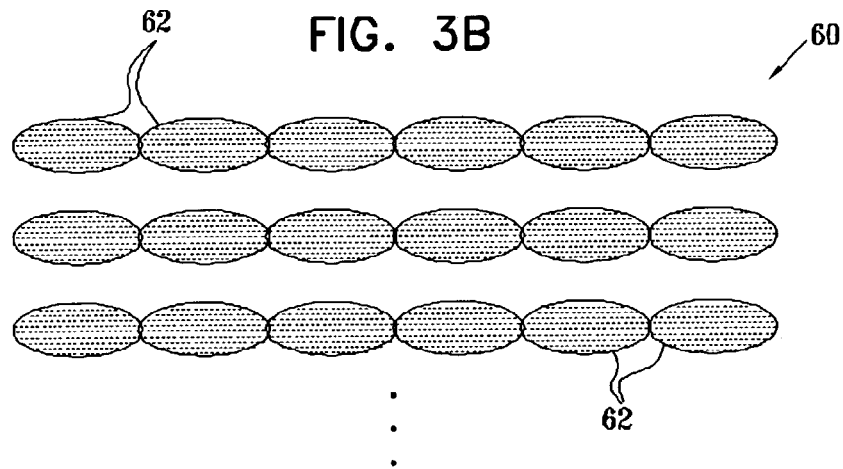
FIG. 3B is a schematic frontal view of an interference pattern created by radiation reflected from a substrate after apodization by the aperture of FIG. 2A.
Figure 3C:
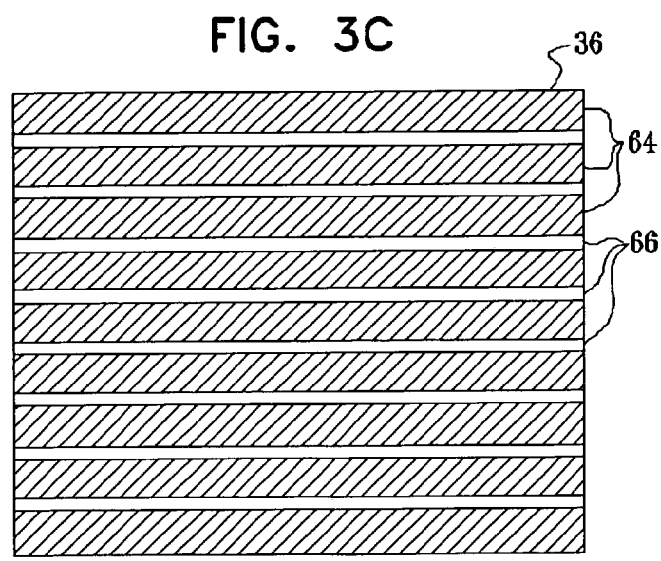
FIG. 3C is a schematic frontal view of a spatial filter used to block the interference pattern of FIG. 3A, in accordance with an embodiment of the present invention.

FIGS. 3B and 3C show further details of the apodization scheme of FIG. 2A, using aperture 50. FIG. 3B shows a pattern 60 of interference lobes 62, created in the Fourier plane of objective 32 due to diffraction from the repetitive structure on substrate 22. Each of lobes 62 in pattern 60 is a spatial Fourier transform of the pattern of spots shown in FIG. 2B. Thus, the shape of lobes 62 is determined by the shape of aperture 50. In the example shown in FIG. 3B, lobes 62 overlap with their neighbors in the horizontal direction, but there is a space between the lobes in the vertical direction.

FIG. 3C shows details of spatial filter 36, which is matched to pattern 60 and takes advantage of the spaces between the rows of lobes 62. Filter 36 comprises alternating opaque stripes 64 and transparent stripes 66. The opaque stripes are aligned so as to block substantially all of the radiation in lobes 62. Radiation scattered from objects on the surface of substrate 22 other than the repetitive pattern, such as radiation scattered from surface defects, is able to pass through transparent stripes 66. Of course, a portion of the radiation scattered from defects is also blocked by opaque stripes 64, so that the defect signal at detector 38 is reduced by filter 36, but the background level, due to lobes 62, is reduced to a much greater extent. Therefore, proper choice of the apodization scheme can give a substantial enhancement of the overall SNR of system 20.

Figure 4A:
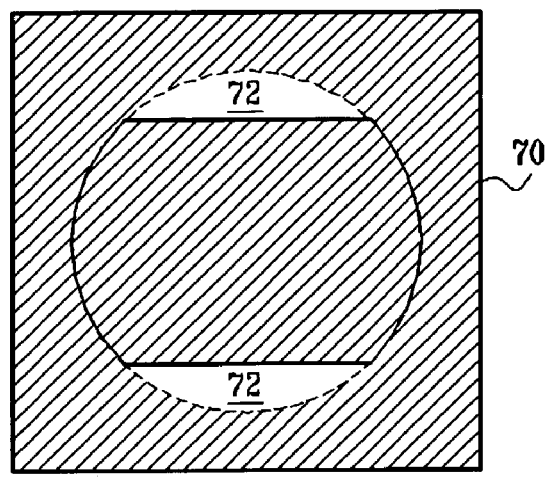
FIG. 4A is a schematic frontal view of an aperture used to apodize a beam of radiation in an optical inspection system, in accordance with another embodiment of the present invention.
Figure 4B:
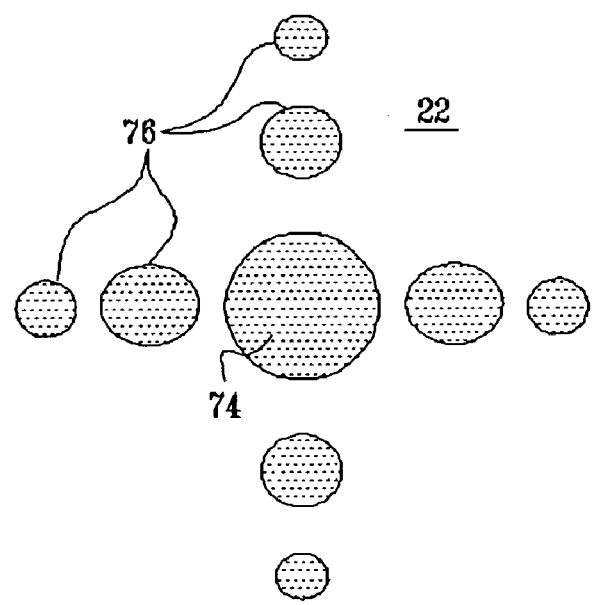
FIG. 4B is a schematic top view of a substrate on which the beam apodized by the aperture of FIG. 4A is incident, showing a pattern of the radiation that is incident on the substrate.

Reference is now made to FIGS. 4A and 4B, which schematically show details of an alternative apodization scheme that can be used in system 20, in accordance with an embodiment of the present invention. FIG. 4A is a schematic frontal view of another aperture 70 that may be used as an apodizer in entrance pupil 30, while FIG. 4B shows a pattern of spots 74 and 76 formed on the surface of substrate 22 due to focusing of the laser beam through aperture 70. In this case, the central, rectangular region of the circular aperture area is blocked, leaving peripheral transparent openings 72. This configuration is referred to herein as a "negative" aperture, in contrast to the "positive" aperture shown in FIG. 2A. The negative shape of aperture 70 causes narrowing of interference lobes 62 at the plane of spatial filter 36, similar to that shown in FIG. 3B. On the other hand, the shape of aperture 70 does not cause vertical elongation of central spot 74 in the pattern of FIG. 4B, unlike central spot 54 in the pattern of FIG. 2B. Rather, central spot 74 maintains the same round, compact shape as it would have if a circular entrance pupil were used. (Peripheral spots 76 are enlarged, however.)

Aperture 70 is advantageous particularly when the pattern on substrate 22 has a particularly high pitch (i.e., repeating features spaced relatively far apart), so that lobes 62 have substantial overlap. In this case, the aperture must be narrow in the vertical direction in order to leave sufficient space between the rows of lobes 62 for the scattered signal to pass through stripes 66. Excessive narrowing of aperture 50 (FIG. 2A) may cause so much elongation of central spot 54 that the ratio of the intensity of the scattered rays from defects on the surface to the background scatter from the pattern, is too far reduced. This problem may be remedied by the use of a negative aperture, such as that shown in FIG. 4A. Although the overall flux of radiation incident on the surface is reduced when the negative aperture is used, the defect signal/background ratio is increased due to the smaller spot size provided by the negative aperture.

Figure 5A:
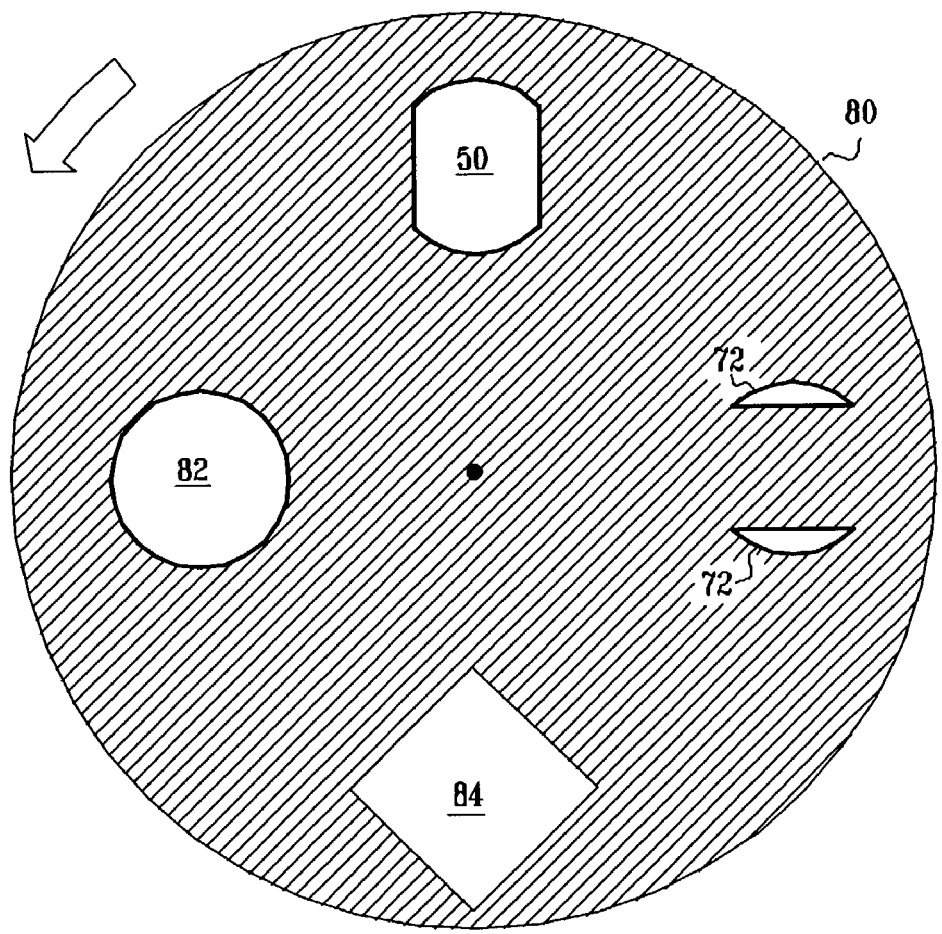
FIG. 5A is a schematic frontal view of a mask wheel, which provides a selection of different apertures, in accordance with an embodiment of the present invention.

FIG. 5A is a schematic frontal view of an aperture wheel 80, providing apertures of different shapes for use in entrance pupil 30, in accordance with an embodiment of the present invention. Wheel 80 may be fabricated using any suitable method known in the art. For example, the wheel may be made of metal with holes shaped to provide the desired apertures. Alternatively, the wheel may be made from a transparent material, such as glass, with an opaque layer, such as chromium, deposited on the glass so as to define the different apertures. Wheel 80 is mounted in system 20 (FIG. 1) at the location of aperture 30 so that the different apertures may be rotated into place. Spatial filter 36 may likewise comprise a wheel with different filtering configurations, or a variable filtering structure, such as a liquid crystal light valve array or a micro-shutter or micro-mirror array. Such arrays are described, for example, in U.S. patent application Ser. No. 10/050,890, filed Jan. 15, 2002, which is assigned to the assignee of the present patent application, and whose disclosure is incorporated herein by reference.

Wheel 80, as shown in FIG. 5A, includes a number of exemplary aperture shapes, including aperture 50 and openings 72, as described above, as well as a conventional circular aperture 82. Additional apertures of different shapes and sizes may be incorporated in the wheel, as well, depending on the characteristics of system 20 and of the substrates that the system is used to inspect.

The orientation of the apertures may be varied, as well, as exemplified by a diagonal aperture 84. An angled aperture of this sort may be useful, for example, in conjunction with an appropriate configuration of spatial filter 36, in blocking interference lobes that arise at certain angles due to particular types and orientations of geometric features on substrate 22. For example, memory chips commonly comprise rows of repeating structures, wherein each row is offset from the one above it. Such a structure gives a pattern of interference lobes similar to that shown in FIG. 3A, except that lobes 62 in successive rows are similarly offset.

Figure 5B:
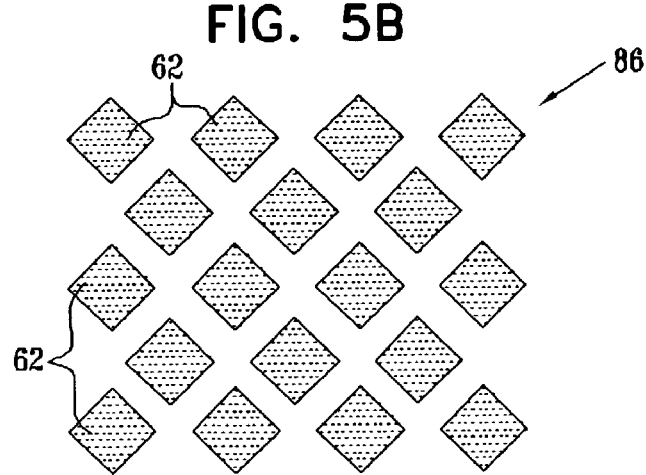
FIG. 5B is a schematic frontal view of an interference pattern created by radiation reflected from a substrate after apodization by one of the apertures in the mask wheel of FIG. 5A.

FIG. 5B is a schematic frontal view of a pattern 86 of lobes 62 that is obtained from this sort of offset periodic structure when incident beam 27 is apodized by aperture 84. The square or rhomboid shape of lobes 62 in this embodiment reflects the shape of the aperture. In order to block the background light in lobes 62 in this case, filter 36 (as shown in FIG. 3C) may be rotated to a diagonal orientation in which stripes 66 are aligned with the clear areas between lobes 62. Alternatively, other spatial filtering schemes may be used, as will be apparent to those skilled in the art.

The apodization scheme in system 20 may be adapted to reduce noise due not only to diffraction from periodic patterns on substrate 22, but also to other sources of non-homogeneous scattering. One of these noise sources is granularity noise, which arises due to scattering from minute grains in the surface of substrate 22. The most common cause of this sort of noise is the stochastic granular properties of metallic substances used in producing interconnects in IC wafers. The granularity causes variations in the level of scattered light reaching detector 38, which can obscure the variations of the scattered signal due to actual defects.

To address this problem, in an embodiment of the present invention, a rectangular aperture, such as aperture 50, is used to elongate central spot 54 of the illumination pattern on substrate 22. Typically, the metal lines on the wafer surface run mainly in one predefined direction (particularly in uniform, periodic structures, such as memories). The aperture is oriented so that the long axis of spot 54 is parallel to the metal lines on the surface. Elongating the spot in this manner causes simultaneous scattering from an extended area of any metal line scanned by the spot, so that the granularity noise is averaged over the spot. A similar effect could be achieved simply by symmetrically increasing the diameter of spot 54. As noted above, however, any increase in size of the focal spot on the surface of the substrate leads to a reduction in the ratio of the scattered signal received by detector 38 due to defects on the surface to the background scattering from the surface pattern. Therefore, it is advantageous to enlarge spot 54 only along a single axis, as shown in FIG. 2B, in order to minimize the loss of signal while smoothing the granularity noise.

FIG. 6 is a schematic frontal view of a variable aperture 90, for use at entrance pupil 30, in accordance with another embodiment of the present invention. Aperture 90 comprises an array of shutter elements 92, which can be controlled to adjust the shape of a transparent area 94. Array 90 may comprise, for example, a liquid crystal device or a micromirror or micro-shutter array, such as arrays of the types described in the above-mentioned U.S. patent application Ser. No. 10/050,890. Elements 92 may be opened or closed to generate substantially any desired aperture shape, including those shown in wheel 80.

FIG. 7A is a schematic frontal view of an acousto-optic device 100, which may be used to apodize the laser beam used to scan substrate 22, in accordance with an embodiment of the present invention. Device 100 is configured to serve as a traveling lens, which may also be integrated in scanner 26. An acoustic transducer 102, typically a piezoelectric element, generates acoustic waves 106, which travel through an acousto-optic crystal 104. Transducer 102 is driven so that the acoustic waves are synchronized with the scanning of the laser beam, in such a way that the wave pattern in crystal 104 tracks the laser beam along the primary scan direction, as is known in the art. As the laser beam passes through the crystal, it is cylindrically focused due to the acousto-optic effect engendered by waves 106. The cylindrical focusing caused by device 100 alters the numerical aperture (NA) applied to beam 27 in the primary scan direction, and thus has an equivalent effect to the use of aperture 50 (FIG. 2A) in entrance pupil 30. Other types of light modulators, such as electro-optic modulators, may also be used for this purpose, as well as other focusing devices having a non-uniform NA.

FIG. 7B is a schematic plot of a waveform 107 that is used to drive transducer 102, in accordance with an embodiment of the present invention. Waveform 107 is frequency-chirped, causing a variation in the spatial frequency of waves 106 across the focusing region. The characteristics of waveform 107 thus determine the effective properties of device 100 as a traveling lens. Typically, a conventional cylindrical lens or other focusing element (not shown) is used to focus beam 27 in the direction transverse to the primary scan axis. For circular apodization, a broader waveform 108 is applied to transducer 102, so that the NA applied to beam 27 is the same in both the scan axis and the transverse axis. The reduced duration of waveform 107 causes a reduction of the NA along the scan axis, while maintaining the same focal length as waveform 108. The use of waveform 107 thus gives a similar effect, in terms of the shape of the beam focused on substrate 22, to that of aperture 50.

Although waveform 107 is shown in FIG. 7B to have sharp leading and trailing edges, the amplitude envelope of the waveform may also be controlled to rise and fall off gradually. By appropriately choice of the amplitude envelope, device 100 may be used to effectively smooth the edges of the entrance pupil, and thus to reduce or eliminate the appearance of peripheral spots 56 (FIG. 2B).

Figure 8:
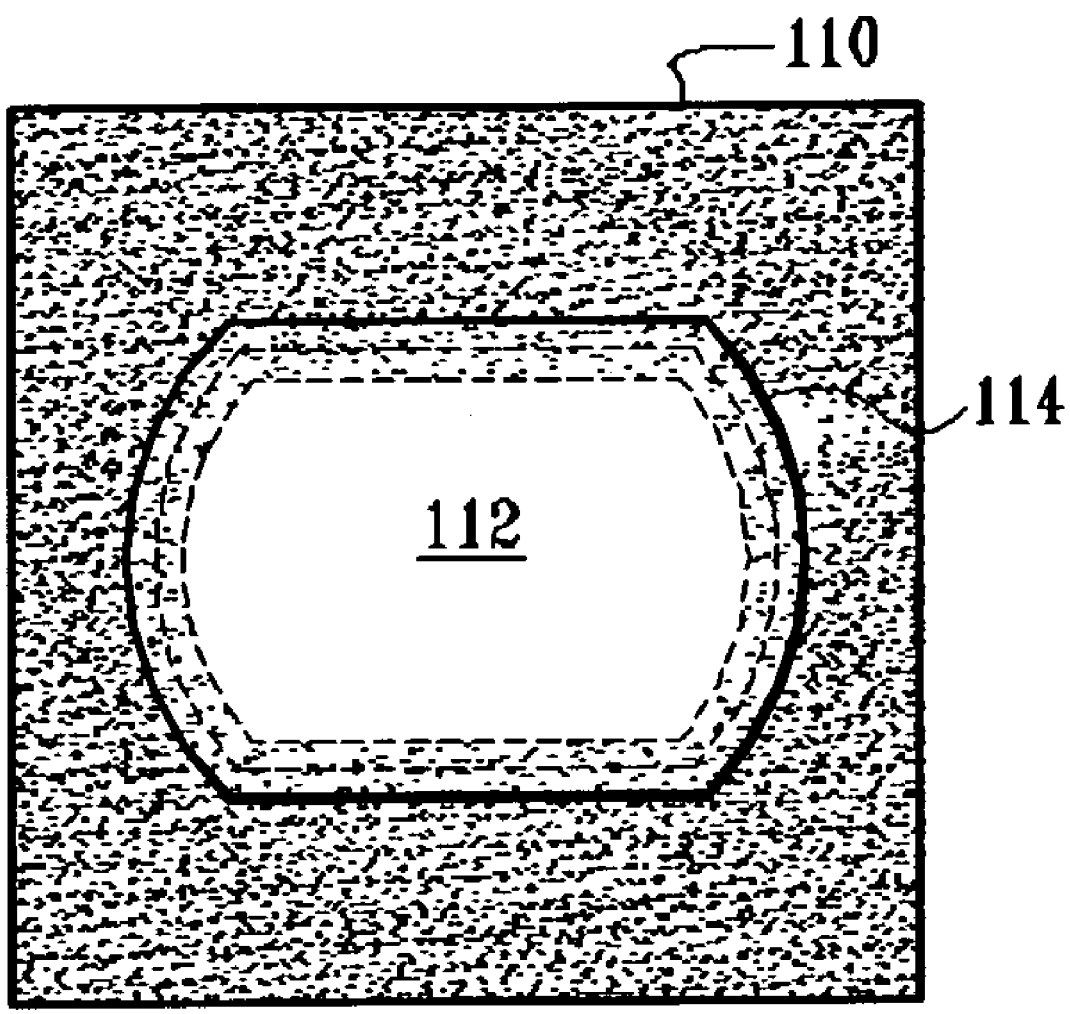
FIG. 8 is a schematic frontal view of an aperture used to apodize a beam of radiation in an optical inspection system, in accordance with another embodiment of the present invention.

FIG. 8 is a schematic frontal view of an aperture 110, for use at entrance pupil 30, in accordance with another embodiment of the present invention. Aperture 110 has a central transparent region 112, surrounded by a transition region 114, whose optical density decreases smoothly from the periphery of the aperture in toward the transparent region. Methods for making optical density filters with smooth variation of density are well known in the art. An advantage of using an aperture with a smooth edge of this sort is that it reduces the intensity of peripheral spots 56 (FIG. 2B) relative to the intensity of central spot 54 on substrate 22. If one of the peripheral spots happens to fall on a highly-scattering area of the substrate, it can substantially increase the noise reaching detector 38. By the use of a Gaussian transmission profile in transition region 114, for example, the intensity of peripheral spots 56 can be reduced to about 0.03% of the intensity of spot 54, as compared with about 1% when sharp aperture edges are used.

Although aperture 110 provides a positive, rectangular entrance pupil, substantially any aperture shape may be produced with smooth edges as shown in FIG. 8. Similarly, some or all of the apertures in wheel 80 (FIG. 5) may have smooth edges of this sort.

Figure 9A:
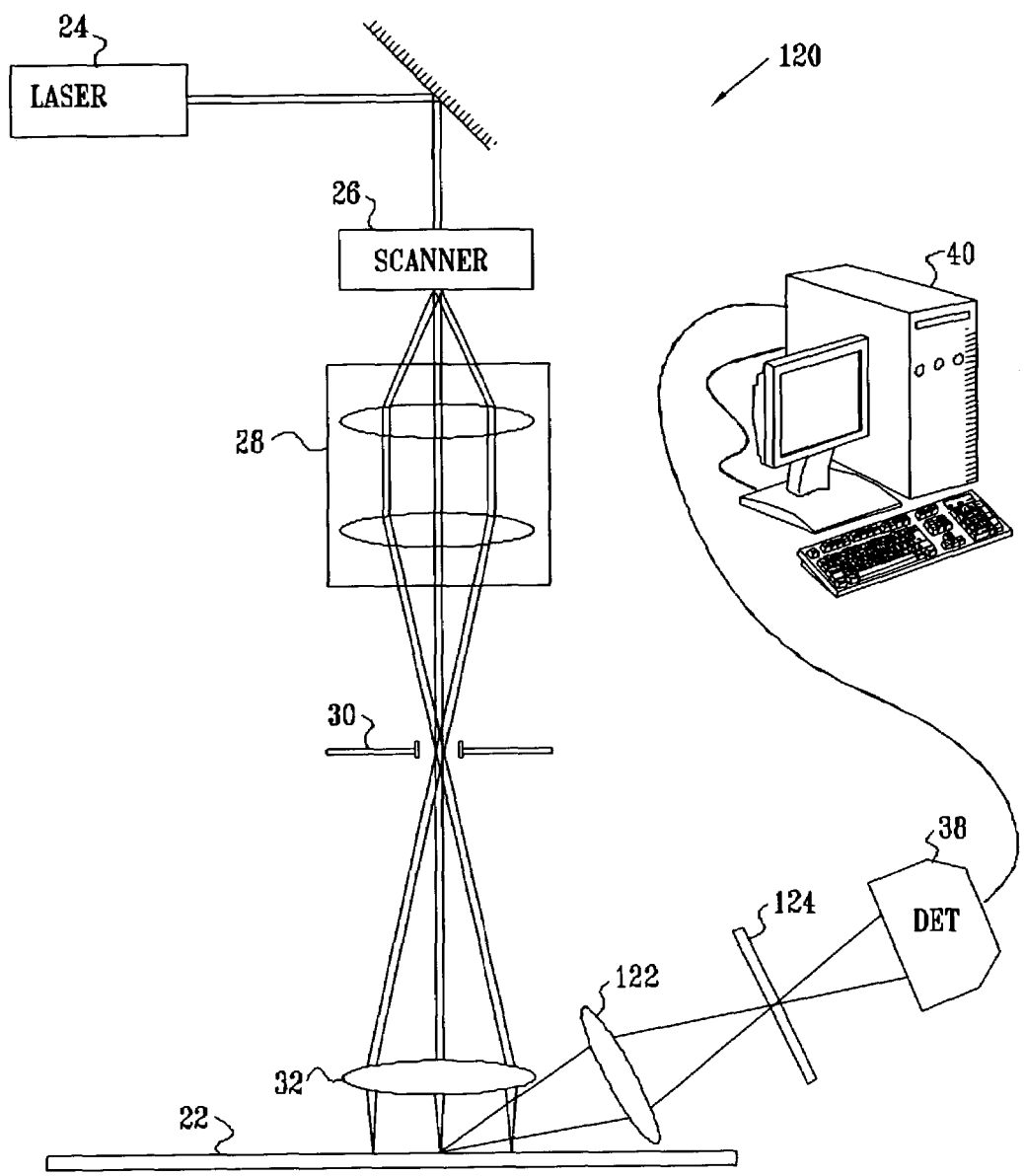
FIGS. 9A and 9B are schematic side views of optical inspection systems, in accordance with further embodiments of the present invention.

FIG. 9A is a schematic side view of a system 120 for optical inspection of substrate 22, in accordance with another embodiment of the present invention. System 120 uses oblique collection of the scattered light, as opposed to the normal collection configuration of system 20. Light scattered from the surface of substrate 22 is collected by a Fourier lens 122, which focuses the scattered light through a spatial filter 124 onto detector 38. In other respects, system 120 is substantially similar in operation to system 20, and the various apodization schemes described above with reference to system 20 may all be applied, mutatis mutandis, in system 120.

Figure 9B:
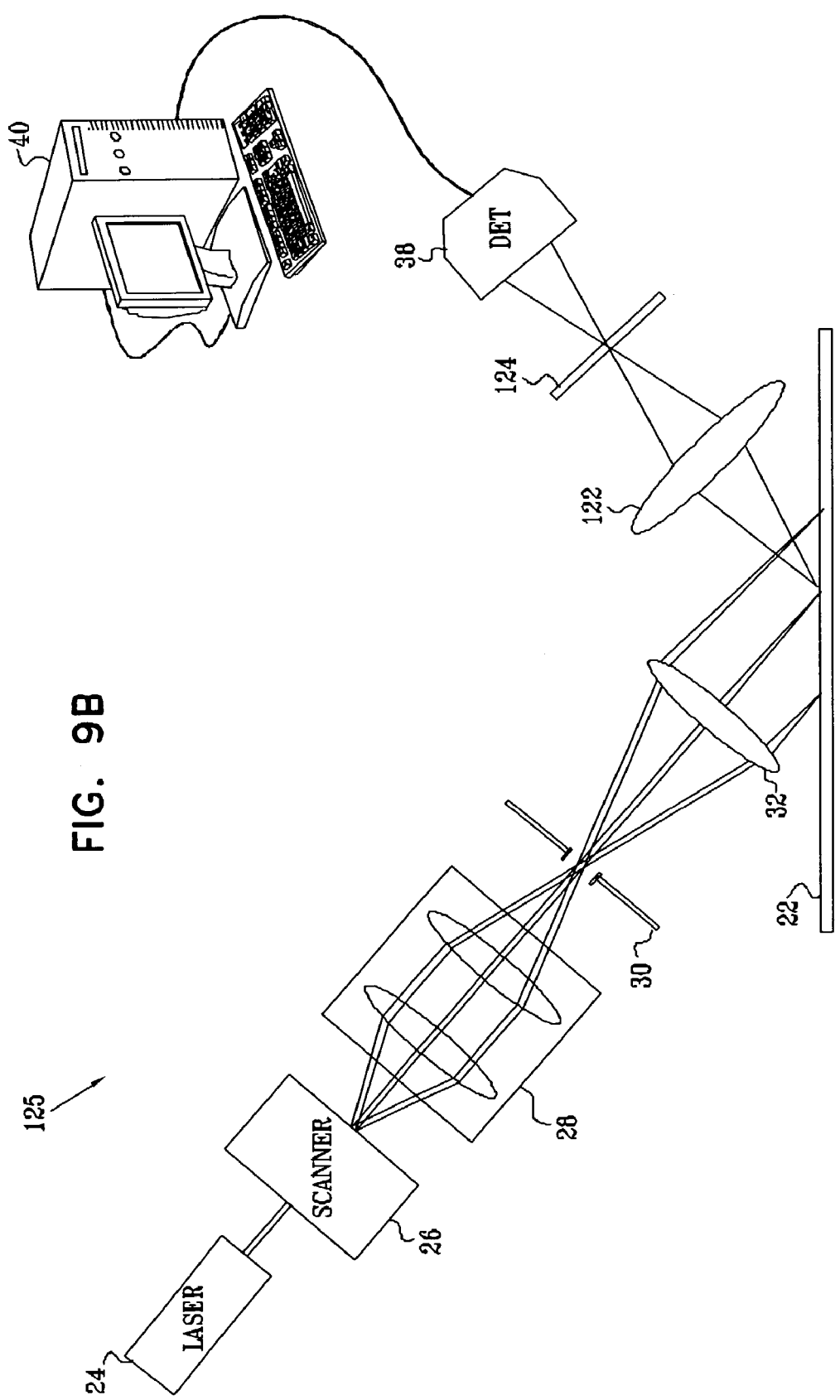

FIG. 9B is a schematic side view of a system 125 for optical inspection of substrate 22, in accordance with yet another embodiment of the present invention. System 125 uses both oblique irradiation of substrate 22 and oblique collection of the scattered light. Alternatively, the principles of the present invention may be applied in similar fashion to systems based on oblique irradiation of substrate 22 by beam 27, with normal collection of the scattered light. All such alternative irradiation and collection configurations will be apparent to those skilled in the art, upon reading the foregoing description, and are considered to be within the scope of the present invention.

Figure 10:
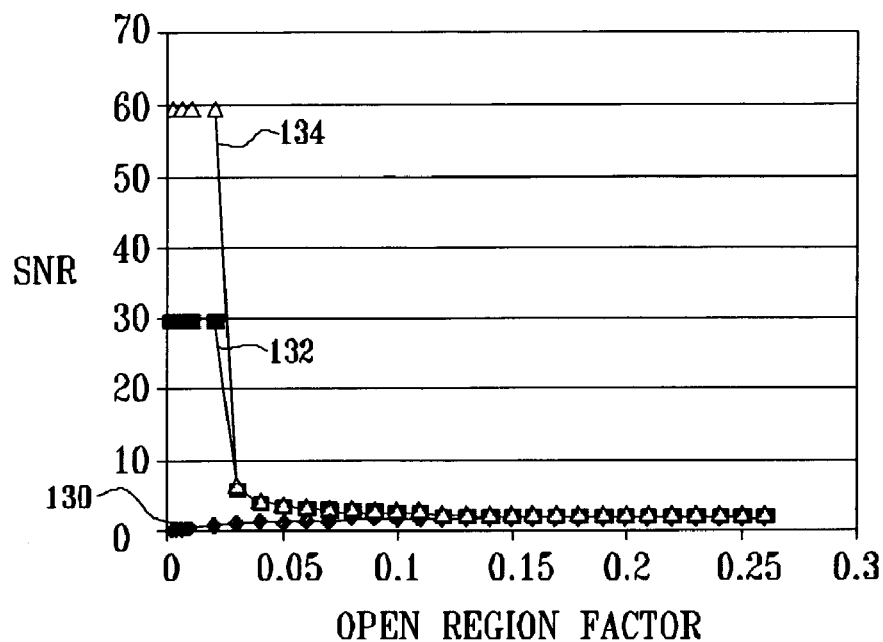
FIGS. 10 and 11 are schematic plots of signal/noise ratio (SNR) for an optical inspection system for different choices of apodization and spatial filtering characteristics, in accordance with embodiments of the present invention.
Figure 11:
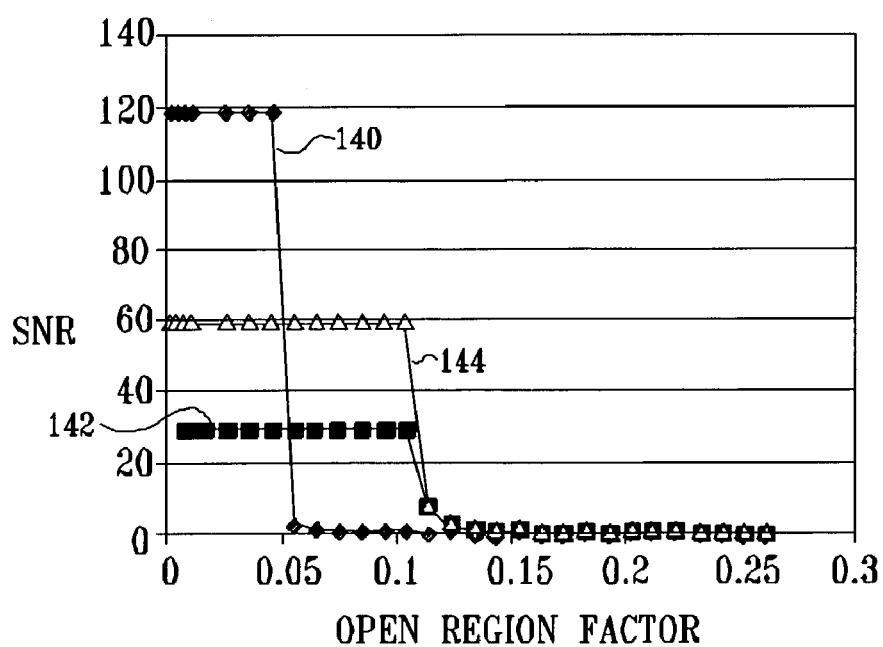

Reference is now made to FIGS. 10 and 11, which are plots of SNR against "open region factor" for a number of different apodization configurations, illustrating operational considerations in application of the present invention. The open region factor is equal to the relative area of spatial filter 36 that is occupied by transparent stripes 66 (FIG. 3B). The SNR is calculated (in arbitrary, relative units) and plotted for three different entrance apertures:

1. A large, circular aperture of diameter D—corresponding to curves 130 in FIGS. 10 and 140 in FIG. 11.
2. A small, circular aperture of diameter $D_Y$—corresponding to curves 132 in FIGS. 10 and 142 in FIG. 11.
3. A positive rectangular aperture, as shown in FIG. 2A, having a long dimension D and a short dimension $D_Y$, corresponding to curves 134 in FIGS. 10 and 144 in FIG. 11.

FIG. 10 shows the SNR calculated assuming a periodic pattern on substrate 22 with a pitch in the horizontal (X) direction $P_X=6$ μm, and a smaller pitch in the vertical (Y) direction $P_Y=3$ μm. In FIG. 11, $P_X=P_Y=3$ μm.

In order to estimate the SNR for a given pattern and optical configuration, we define the following additional terms:

$S_d$—Signal from defect—assuming aperture diameter D (μW).
$S_p$—Signal from repetitive pattern features (μW)/
$S_b$—Wafer background signal variation, which is not due to the repetitive pattern (μW/μm²).
f—Focal length of objective (mm).
λ—Illumination wavelength (μm).
$C_X$—Total collection angle—lateral size in the X angular direction (radians).
$C_Y$—Total collection angle—lateral size in the Y angular direction (radians).
$O_X$—Open collection angle—lateral size in the X angular direction (radians). (Although $O_X=C_X$ in the specific example analyzed below, the present formulation may be applied generally to any reasonable values of these parameters.)
$O_Y$—Open collection angles (due to transparent stripes 66)—lateral size in the Y angular direction (radians).

To estimate the SNR for the apodization patterns in question, we first calculate the spot size on the substrate for the three different apertures mentioned above:

Spot size for aperture 1: $S_1=2*0.82*\lambda*f/D$.
Spot size for aperture 2: $S_2=2*0.82*\lambda*f/D^Y$.
Spot size on wafer in X direction for aperture 3: $S_{3X}=2*0.82*\lambda*f/D$.
Spot size on wafer in Y direction for aperture 3: $S_{3Y}=2*0.82*\lambda*f/D_Y$.

The spot areas for the different cases are then given as follows:

Spot area on substrate for aperture 1: $A_1=(\pi S_1^2)/4$.
Spot area on substrate for aperture 2: $A_2=(\pi S_2^2)/4$.
Spot area on substrate for aperture 3: $A_3=(\pi S_{3X}*S_{3Y})/4$.

Using these values, we can now estimate the scattering signal reaching detector 38 from a defect on substrate 22 for the three different cases. The signal strength depends on the intensity of illumination on the wafer, which decreases as the area of the spot increases and as the entrance pupil area decreases. The signal strength at the detector is also proportional to the open region of filter 36. The usable open region depends on the pitches of the repetitive pattern ($P_X$ and $P_Y$) and on the shape and size of the entrance pupil. For the purpose of this estimate, we assume $P_X>>P_Y$, as is the usual case for most DRAM and SRAM structures, so that filter 36 has the general form shown in FIG. 3B. We then find the following signal levels:

Signal reaching detector 38 from the defect using aperture 1: $SIG_1=S_d*O_Y/C_Y$.
Signal reaching detector 38 from the defect using aperture 2: $SIG_2=S_d*A_2/A_1*O_Y/C_Y$.
Signal reaching detector 38 from the defect using aperture 3: $SIG_3=S_d*A_3/A_1*O_Y/C_Y$.

It can be seen that the signal at detector 38 decreases as the entrance pupil size decreases—quadratically in the case of aperture 2, and linearly in the case of aperture 3.

The noise has two components: The first is noise arising due to scattering from the repetitive pattern, which decreases as the entrance pupil shrinks, but remains practically constant as the spot area increases. The insensitivity to spot area is due to the fact that as the spot area increases, the intensity density decreases, but the number of periodic scatterers interacting with the spot increases by the same factor:

Noise due to the repetitive pattern for aperture 1: $NR_1=SP*A_1/(P_X*P_Y)*\min[0,[O_Y-\lambda(1/P_X-D/f)]/C_Y]$.
Noise due to the repetitive pattern for aperture 2: $NR_2=S_p*A_2/(P_X*P_Y)*\min[0,[O_Y-\lambda(1/P_X-D_Y/f)]/C_Y]$.
Noise due to the repetitive pattern for aperture 3: $NR_2=S_p*A_3/(P_X*P_Y)*\min[0,[O_Y-\lambda(1/P_X-D_Y/f)]/C_Y]$.

The "min" term in these equations takes into account the width of the diffraction lobes in the Y-direction (as shown in FIG. 3A) relative to the width of opaque stripes 64 in the spatial filter. It determines whether the lobes are completely blocked by the opaque stripes, or whether a portion of the rays in these lobes penetrates to the detector through transparent stripes 66.

The second noise component is general background noise, which depends on the open region factor ($O_Y/C_Y$):

General background noise for aperture 1: $NB_1=S_b*A_1*O_Y/C_Y$.
General background noise for aperture 2: $NB_2=S_b*A_2*O_Y/C_Y$.
General background noise for aperture 3: $NB_3=S_b*A_3*O_Y/C_Y$.

The SNR for the three different apertures is given by $SNR_i=SIG_i/(NR_i+NB_i)$, wherein i=1, 2, 3. This value depends on $O_Y$, as shown in the equations above and illustrated in FIGS. 10 and 11. As seen in FIG. 10, for the typical case of $P_X=6$ μm and $P_Y=3$ μm, aperture 3—the rectangular aperture, represented by curve 134—gives superior SNR to both of the circular apertures that were evaluated. On the other hand, for the very small pitch used in FIG. 11, with $P_X=P_Y=3$, a circular aperture—curve 140—gives superior results, as long as a very small open region factor is used. Under some circumstances, however, it may be desirable to use a larger open region factor, in which case the rectangular aperture—curve 144—is superior.

Although certain apodization schemes are described hereinabove with reference to particular inspection systems 20 and 120, the principles of the present invention may be applied to other types of optical inspection systems, using such alternative apodization schemes as will be apparent to those skilled in the art. It will thus be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. A method, comprising:
   directing a beam of radiation towards a patterned surface of a sample, said patterned surface having a substantially regular pattern;
   subjecting said beam to a selected apodization scheme before it impinges on said patterned surface to produce an apodized beam having shape and angle of incidence characteristics determined by the selected apodization scheme, said selected apodization scheme determined by an apodizer and at least in part by a spatial filter, each chosen from among a plurality of available shapes set in respective wheels, wherein the apodizer adjusts an angle of incidence of the beam on the surface;
   impinging the apodized beam onto the patterned surface so as to produce scattered radiation from the patterned surface, a first portion of said scattered radiation resulting from impingement of the apodized beam on the substantially regular pattern and a second portion resulting from impingement of the apodized beam on defects in the substantially regular pattern;
   filtering said first portion of said scattered radiation with the spatial filter matched to said selected apodization scheme so as to suppress scattered interference lobes created by impingement of the apodized beam on the substantially regular pattern; and
   detecting with a detector at least some of said second portion of said scattered radiation.

2. The method according to claim 1, wherein the selected apodization scheme comprises a selected characteristic of an entrance pupil, and the beam of radiation is passed through the entrance pupil.

3. The method according to claim 2, wherein the selected characteristic of the entrance pupil comprises a non-circular entrance pupil.

4. The method according to claim 3, wherein the non-circular entrance pupil is provided by placing an aperture having a generally rectangular shape in the entrance pupil.

5. The method according to claim 3, wherein the non-circular entrance pupil is provided by placing a negative aperture in the entrance pupil.

6. The method according to claim 3, wherein the non-circular entrance pupil is provided by placing an aperture having edges characterized by a smooth gradation of optical density in the entrance pupil.

7. The method according to claim 3, wherein the non-circular entrance pupil is provided by placing in the entrance pupil an aperture having a length dimension and a width dimension, wherein the length and width dimensions are not equal.

8. The method according to claim 7, wherein at least one of the length and width dimensions is set in response to a pitch of the substantially regular pattern.

9. The method according to claim 2, wherein the selected characteristic of the entrance pupil comprises an offset of the entrance pupil relative to an axis of the beam of radiation so as to adjust the angle of incidence of the apodized beam on the surface.

10. The method according to claim 2, wherein the selected characteristic of the entrance pupil comprises a choice of one of a plurality of apertures to place in the entrance pupil.

11. The method according to claim 1, wherein the apodization scheme is selected so as to limit an angular extent of the lobes.

12. The method according to claim 11, wherein an attribute of the apodization scheme is set in response to a pitch of the substantially regular pattern.

13. The method according to claim 1, wherein detecting at least some of said second portion of radiation comprises measuring the second portion of radiation to identify a defect in the substantially regular pattern.

14. The method according to claim 1, further comprising scanning the apodized beam of radiation over the surface, and wherein detecting the at least some of the second portion of radiation comprises detecting radiation scattered from multiple points on the surface scanned by the apodized beam of radiation.

15. The method according to claim 14, wherein the apodization scheme comprises an optical modulator and apodizing comprises driving the optical modulator in synchronization with scanning the apodized beam.

16. The method according to claim 1, wherein the apodization scheme comprises an apodizer having a non-uniform numerical aperture (NA) and subjecting the beam to the selected apodization scheme comprises focusing the beam of radiation onto the surface with a first NA along a first transverse axis and a second NA along a second transverse axis, perpendicular to the first transverse axis, such that the first NA is substantially different from the second NA.

17. The method according to claim 1, wherein the apodized beam irradiates the surface in at least one of a normal incidence direction and an oblique incidence direction.

18. The method according to claim 1, wherein detecting the at least some of the second portion of radiation comprises configuring the detector to receive the at least some of the second portion of radiation in a dark field detection configuration, along at least one of a normal collection axis and an oblique collection axis.

19. An apparatus, comprising:
   a radiation source, adapted to generate a beam of coherent radiation;
   a first wheel including a plurality of apodizers of different shapes, each apodizer adapted to apodize the beam according to a selected apodization scheme affecting a shape and adjusting an angle of incidence of the beam to produce an apodized beam of radiation;
   an optical objective, adapted to direct the apodized beam of radiation to impinge on a patterned surface of a sample, said patterned surface having a substantially regular pattern so as to produce scattered radiation from the patterned surface, a first portion of said scattered radiation resulting from impingement of the apodized beam on the substantially regular pattern and a second portion of said scattered radiation resulting from impingement of the apodized beam on defects in the substantially regular pattern;
   a second wheel including a plurality of spatial filters, each matched to a respective one of said apodizers so as to suppress scattered interference lobes created by impingement of the apodized beam on the substantially regular pattern; and a detector, adapted to detect at least some of said second portion of said scattered radiation.

20. The apparatus according to claim 19, wherein each of the apodizers comprises an entrance pupil, through which the beam of radiation passes before impinging on the scattered surface, and wherein the entrance pupil has a characteristic that is controllable in response to the selected apodization scheme.

21. The apparatus according to claim 20, wherein the entrance pupil comprises a non-circular aperture.

22. The apparatus according to claim 21, wherein the aperture has a generally rectangular shape.

23. The apparatus according to claim 21, wherein the aperture comprises a negative aperture.

24. The apparatus according to claim 21, wherein the aperture has a length dimension and a width dimension such that the length and width dimensions are not equal.

25. The apparatus according to claim 24, wherein at least one of the length and width dimensions is selected in response to a pitch of the substantially regular pattern on the surface.

26. The apparatus according to claim 20, wherein the entrance pupil has an offset relative to an axis of the beam of radiation, and wherein the offset is adjustable so as to adjust the angle of incidence of the beam on the surface.

27. The apparatus according to claim 20, wherein the entrance pupil comprises an aperture having edges characterized by a smooth gradation of optical density.

28. The apparatus according to claim 20, wherein at least one of the apodizers comprises a plurality of apertures, said apodizers being adapted to be selectably placed in the entrance pupil.

29. The apparatus according to claim 19, wherein the apodizers are selectable so as to limit an angular extent of the lobes.

30. The apparatus according to claim 29, wherein the apodizers are selectable in response to a pitch of the substantially regular pattern.

31. The apparatus according to claim 19, wherein the detector is adapted to generate a signal in response to the at least some of said second portion of said scattered radiation, and further comprising a processor adapted to measure the signal in order to identify a defect in the substantially regular pattern.

32. The apparatus according to claim 19, and comprising a scanner adapted to scan the apodized beam over the surface, and wherein the detector is adapted to detect the at least some of said second portion of said scattered radiation from multiple points on the surface scanned by the beam.

33. The apparatus according to claim 19, wherein at least one of the apodizers comprises a focusing device having a non-uniform numerical aperture (NA) adapted to cause the beam of radiation to be focused onto the surface with a first NA along a first transverse axis and a second NA along a second transverse axis, perpendicular to the first transverse axis, such that the first NA is substantially different from the second NA.

34. The apparatus according to claim 19, wherein the radiation source and optical objective are configured to direct the beam to irradiate the surface in at least one of a normal incidence direction and an oblique incidence direction.

35. The apparatus according to claim 19, wherein the detector is configured to receive the at least one of the scattered rays in a dark field detection configuration, along at least one of a normal collection axis and an oblique collection axis.

* * * * *